United States Patent
Diemeer et al.

(10) Patent No.: US 8,971,672 B2
(45) Date of Patent: Mar. 3, 2015

(54) INTEGRATED OPTICAL WAVEGUIDE EVANESCENT FIELD SENSOR AND LONGITUDINAL SECTION OF A SUBSTRATE FOR USE IN SUCH A SENSOR

(75) Inventors: Martinus Bernardus Johannes Diemeer, Limmen (NL); Hermanus Marcellinus Maria Klein Koerkamp, Enschede (NL); Tonnis Meindert Koster, Enschede (NL)

(73) Assignee: Optisense B.V., Enschede (NL)

( * ) Notice: Subject to any disclaimer, the term of this patent is extended or adjusted under 35 U.S.C. 154(b) by 0 days.

(21) Appl. No.: 13/704,509

(22) PCT Filed: Jun. 15, 2011

(86) PCT No.: PCT/EP2011/059971
§ 371 (c)(1),
(2), (4) Date: Feb. 22, 2013

(87) PCT Pub. No.: WO2011/157766
PCT Pub. Date: Dec. 22, 2011

(65) Prior Publication Data
US 2013/0156363 A1 Jun. 20, 2013

(30) Foreign Application Priority Data
Jun. 17, 2010 (EP) .................................. 10166404

(51) Int. Cl.
*G02B 6/00* (2006.01)
*G01N 21/00* (2006.01)
*G01N 21/77* (2006.01)

(52) U.S. Cl.
CPC ............ *G01N 21/00* (2013.01); *G01N 21/7703* (2013.01); *G01N 2201/0245* (2013.01)

USPC .................................................. 385/12; 435/6

(58) Field of Classification Search
CPC ................ G02B 2006/12147; G01N 21/7703; G01N 21/648; G01N 21/7716
USPC ............................ 385/12, 30, 129, 131; 435/6
See application file for complete search history.

(56) References Cited

U.S. PATENT DOCUMENTS

| 2004/0239944 A1 | 12/2004 | Shirai et al. |
| 2005/0201660 A1* | 9/2005 | Grot et al. ........................ 385/12 |
| 2008/0008418 A1 | 1/2008 | Smith et al. |
| 2009/0068668 A1 | 3/2009 | Duer |
| 2010/0065726 A1 | 3/2010 | Zhong et al. |

FOREIGN PATENT DOCUMENTS

| EP | 1918695 | 5/2008 |
| WO | 9205429 | 4/1992 |

* cited by examiner

*Primary Examiner* — Ryan Lepisto
*Assistant Examiner* — Erin Chiem
(74) *Attorney, Agent, or Firm* — Edward J. Baba; Bozicevic, Field & Francis LLP (57) ABSTRACT

The invention relates to an integrated optical waveguide evanescent field sensor (1) for sensing of chemical and/or physical quantities, comprising a substrate (2) carrying a waveguide layer structure provided with—a waveguide core layer (10) sandwiched between two cladding layers (11, 12) formed by a lower (11) and a upper (12) cladding layer, of a lower refractive index than the waveguide core layer (10), —a sensing section (14A, 14B) comprising a sensing layer (13) included in the upper cladding layer (12), wherein a longitudinal section of said substrate including said waveguide layer structure and said sensing section (14A, 14B) is exchangeable as a separate element (20).

11 Claims, 11 Drawing Sheets

INTEGRATED OPTICAL WAVEGUIDE EVANESCENT FIELD SENSOR AND LONGITUDINAL SECTION OF A SUBSTRATE FOR USE IN SUCH A SENSOR

The invention relates to an integrated optical waveguide evanescent field sensor for sensing of chemical and/or physical quantities, comprising a substrate carrying a waveguide layer structure comprising a waveguide core layer sandwiched between two cladding layers formed by a lower and a upper cladding layer, of a lower refractive index than the waveguide core layer, and a sensing section comprising a sensing layer included in the upper cladding layer.

Integrated optical waveguide evanescent field sensors can be used for sensing of chemical and/or physical quantities. During use, the sensor is usually connected to a measuring device with use of an optical fiber, wherein the optical fiber is optically connected to the waveguide core layer. A disadvantage of the known sensor is that sensing usually needs to be done by skilled persons.

It is an object of the invention to obviate this disadvantage in the sense that an integrated optical waveguide evanescent field sensor is provided wherein sensing can be done by any unskilled person.

In order to accomplish that objective, an integrated optical waveguide evanescent field sensor of the kind referred to in the introduction is characterized in that a longitudinal section of said substrate including said waveguide layer structure and said sensing section is exchangeable as a separate element.

By having the sensing section of the sensor in a separate element, the sensing of chemical and/or physical quantities can easily be done by an unskilled person. For example, this is due to that only said separate element is exchanged for a new sensing session, such that any optical fiber connected to said sensor may remain connected to the remaining parts of said sensor. Since the connection of the sensor with the optical fiber is very precise, such that only skilled person can normally connect the sensor with the optical fiber, this allows for the sensing to be done by any (un)skilled person.

With sensors for sensing of chemical and/or physical quantities care must be taken that cross contamination of different sensors does not occur. Because of the separate sensing section according to the invention, cross contamination can be prevented because a sensing section can be disposed after said sensing is done.

Another advantage is that a separate element allows for manufacturing the separate element apart from said sensor, thereby allowing more freedom of production and/or reduction of the production costs. Also, at the production site the separate element may be wrapped in such a way that it is protected from the environment. In this way contamination of the sensing section of the sensor can be prevented.

Normally, the sensing layer must be applied to the sensor in a controlled environment, and therefore, also sensing normally takes place in the controlled environment. With the sensing layer included in the separate element according to the invention, only said separate element is manufactured in a controlled environment. After manufacturing, the separate element with the sensing layer can be used anywhere, such that sensing can easily take place outside the controlled environment. This allows for more freedom of use of the sensor according to the invention.

Also, said separate element allows for the possibility to exchange the element for a different kind of element, such that different types of sensing can easily be done, without the need to replace the sensor completely. Therefore, the flexibility of use of the sensor according to the invention is enhanced.

It is noted that a longitudinal section is understood such that the separate section extends in the propagation direction of the light travelling through said sensor during use.

The separate element can preferably be located near a midzone or an endzone of said sensor. A separate element that is located near the midzone is preferred if optical fibers are connected to both endzones of said sensor.

In a preferred embodiment of the sensor according to the invention the waveguide layer structure is formed as a channel over a portion of its length. Such a channel has the advantage that light travelling through said sensor during use can be guided accurately.

Preferably, at least one lens is included in the waveguide layer structure located outside said channel and outside said separate element, such that in use a diverging beam leaving the channel and passing through the lens is converted into a parallel beam, which parallel beam has a width that is larger than the width of the channel. An increase in said width of said beam may decrease the accuracy with which the separate element must be positioned. Therefore, exchanging the separate element may become easier.

In another preferred embodiment of the sensor according to the invention, said waveguide layer structure is formed as two parallel channels over said portion of its length, wherein two lenses are included in the waveguide layer structure located outside the channels and outside the separate element, such that in use two diverging beams leaving the two channels and passing through respective lenses are converted into parallel beams, which parallel beams have a width that is larger than the width of the channels. Two parallel channels with lenses for forming two parallel beams have the advantage, that the second parallel channel can be used for multiple purposes. For example, only the first channel may comprise a sensing section comprising a sensing layer, such that the second channel functions as a reference channel. In another embodiment, both channels may comprise sensing sections comprising a sensing layer. With such an embodiment, multiple sensing may be done, wherein different analyte molecules may be sensed. Also, the sensing of the same analyte molecules may be done at both sensing sections, such that the accuracy of the measurements may be improved. Further, one of the sensing layers may be chemically insensitive, such that this channel functions as the reference channel, wherein the accuracy of the reference channel is improved with respect to a reference channel with no sensing layer.

In a practical configuration of the sensor according to the invention, said substrate comprises a splitter for optically splitting a common input channel into said first and second channels at a first junction.

In yet another preferred embodiment of the sensor according to the invention said waveguide layer structure is formed as two parallel third and fourth channels over a second portion of its length, wherein a third lens and a fourth lens are included in the waveguide layer structure located outside the channels and outside the separate element, such that in use the two parallel beams passing through respective lenses are converted into converging beams entering said third and fourth channels.

Practically, said substrate comprises a combiner for optically coupling said third and fourth channels into a common output channel at a second junction.

In a preferred embodiment of the sensor according to the invention, the core layer in the separate element includes a second core layer with tapered endzones. An advantage of such a second core layer with tapered endzones is that this may support the coupling of the light leaving the remaining part of the sensor into the separate element, while sensing may be improved. For correct coupling with minor light losses, the core layers preferably are in line and preferably have the same thickness, such that the profile of the light wave does not chance. It is clear, that a core layer with a larger thickness supporting a light wave with a larger profile can be more easily placed in line with another core layer, than core layers with a smaller thickness supporting a light wave with a more confined profile. However, a core layer with an increased thickness is not optimal for sensing, because the part of the wave that extends in the sensing layer is relatively small. Therefore, for optimal sensing, a core layer with a small thickness is preferred. In the embodiment of the sensor according to the invention, correct coupling may be enhanced by having one core layer that extends from the remaining part of the sensor through the separate element, while sensing is enhanced by the second core layer with tapered endzones included in the separate element. The tapered enzones enhance the guiding of the light into the second core layer.

In another preferred embodiment of the sensor according to the invention the lower cladding layer of at least the separate element has a refractive index that is lower than the refractive index of the upper cladding layer and/or the sensing layer. In particular, the refractive index of the lower cladding layer may be lower than that of the sensing layer. An advantage of a lower cladding layer with a lower refractive index than that of the upper cladding layer is that this enhances the coupling of the light leaving the remaining part of the sensor into the separate element, while sensing may be improved. As explained above, for optimal coupling the profile of the light wave should not chance in the transfer from the remaining part of the sensor into the separate element, which can be achieved by having the core layers in line and with the same thickness. By having a lower cladding layer with a lower refractive index than that of the upper cladding layer, the part of the light extending into the upper cladding layer is enlarged with respect to the light extending into the lower cladding layer. Therefore, in this embodiment, the core layer in the separate element may have a smaller thickness than the core layer in the remaining parts, because the profile of the light extending into the upper cladding layer is expanded, thereby enhancing the coupling of the light. In addition, the sensing accuracy may be improved, because the part of the light extending into the sensing layer is increased.

In a practical configuration of said sensor according to the invention is said substrate formed by said lower cladding layer as one integral part.

The invention further relates to a longitudinal section of a substrate for use in an integrated optical waveguide evanescent field sensor for sensing of chemical and/or physical quantities, said sensor comprising a substrate carrying a waveguide layer structure provided with
 a waveguide core layer sandwiched between two cladding layers formed by a lower and a upper cladding layer, of a lower refractive index than the waveguide core layer,
 a sensing section comprising a sensing layer included in the upper cladding layer, wherein said longitudinal section of said substrate including said waveguide layer structure and said sensing section is exchangeable as a separate element.

The invention will now be explained in more detail with reference to figures illustrated in a drawing, wherein.

Figure 1A:
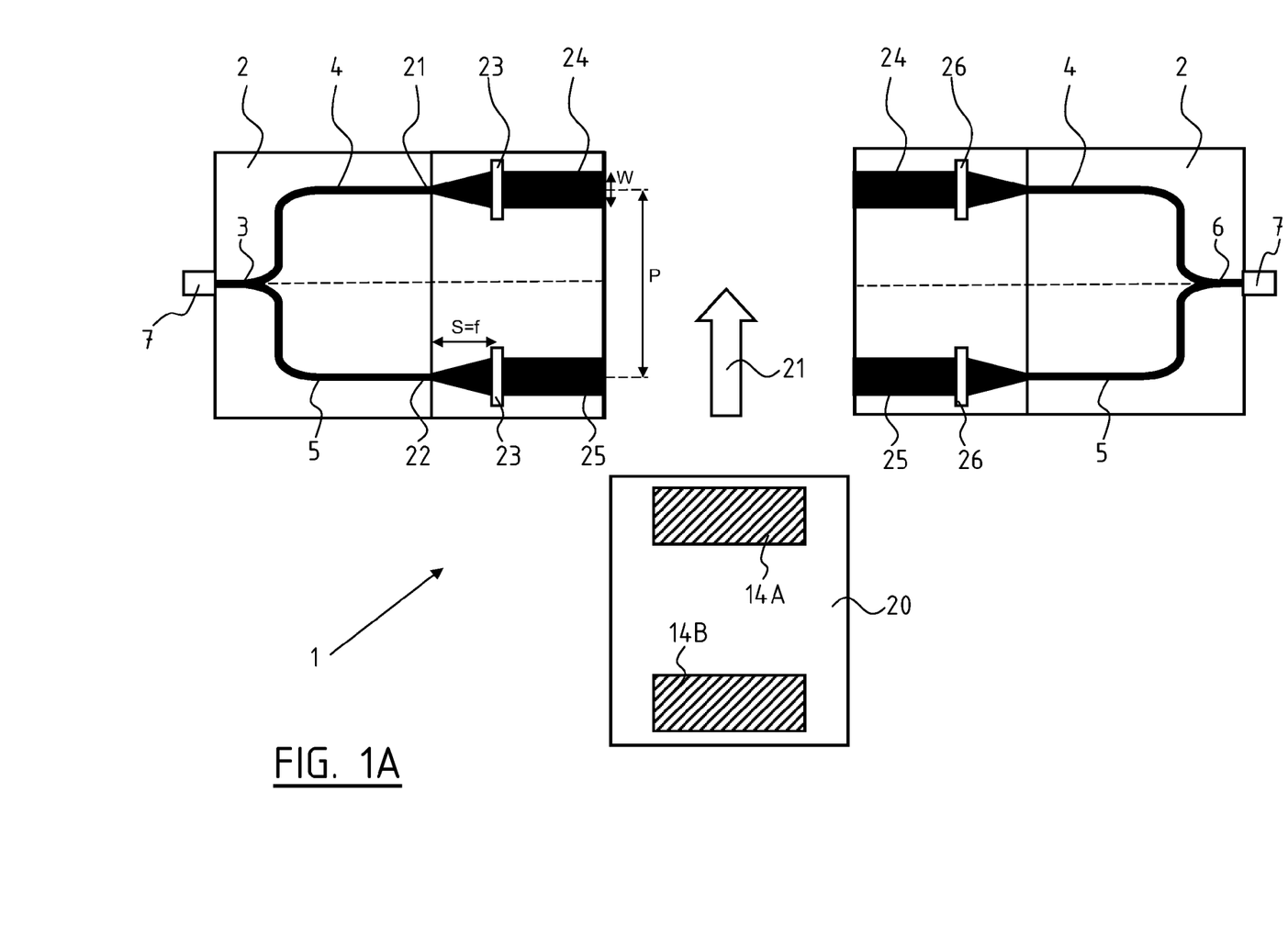
FIGS. 1A, 1B are a top view of a first embodiment of the sensor according to the invention, wherein a longitudinal section is shown separate from the sensor (1A) or in mounted position near a midzone of the sensor (1B)
Figure 1B:
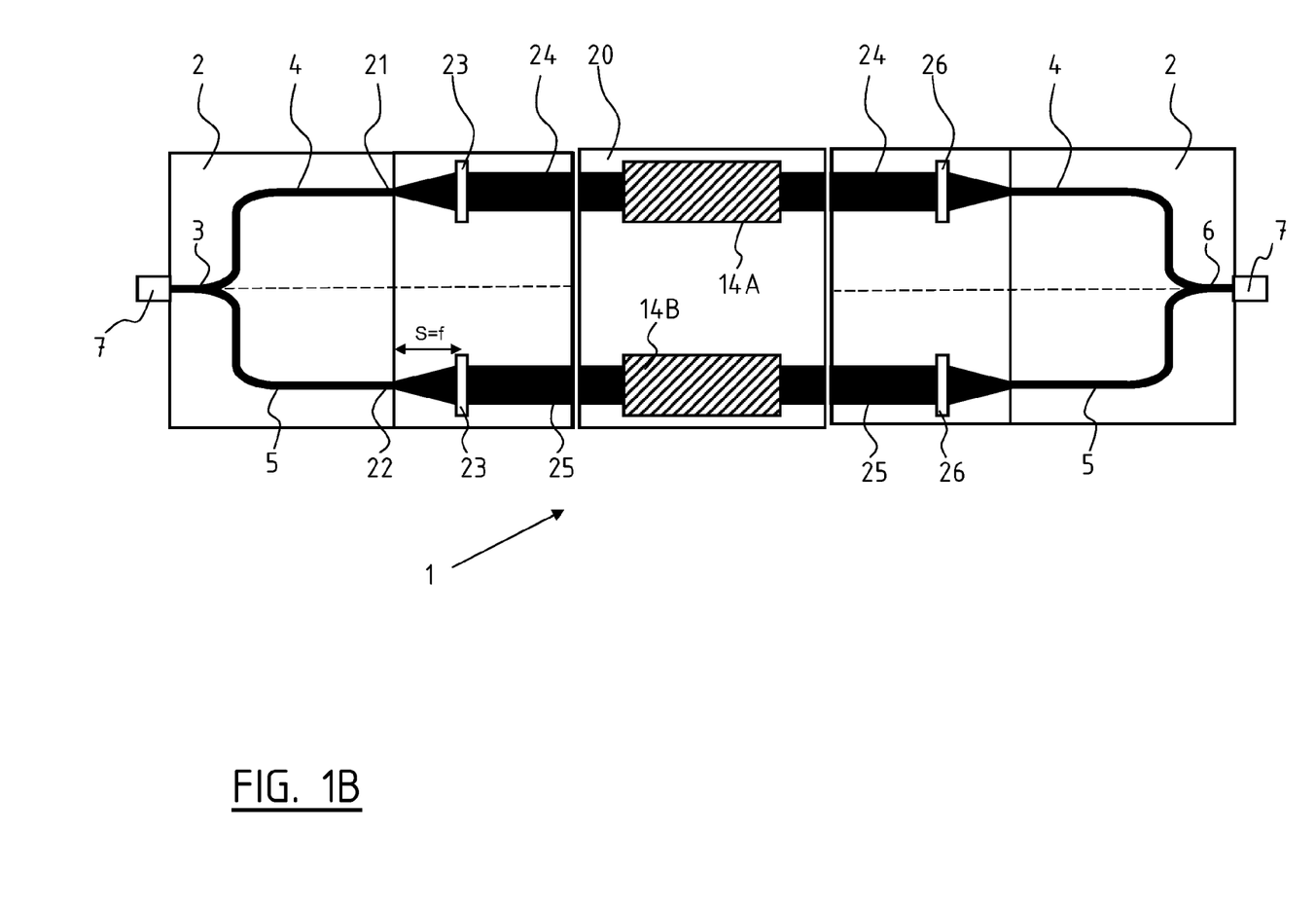

The integrated optical waveguide evanescent field sensor 1 of FIGS. 1A and 1B consists of a substrate 2 carrying a waveguide layer structure in the form of an input channel waveguide 3 that splits up in two parallel branches 4, 5. After a well-defined length, these two parallel branches 4, 5 are combined again to form the output waveguide 6. Light that enters the input waveguide 3 splits equally over the two branches 4, 5 and combines again at the output waveguide 6. Coupled to both the input channel waveguide 3 and the output waveguide 6 are optical fibers 7.

Figure 2A:
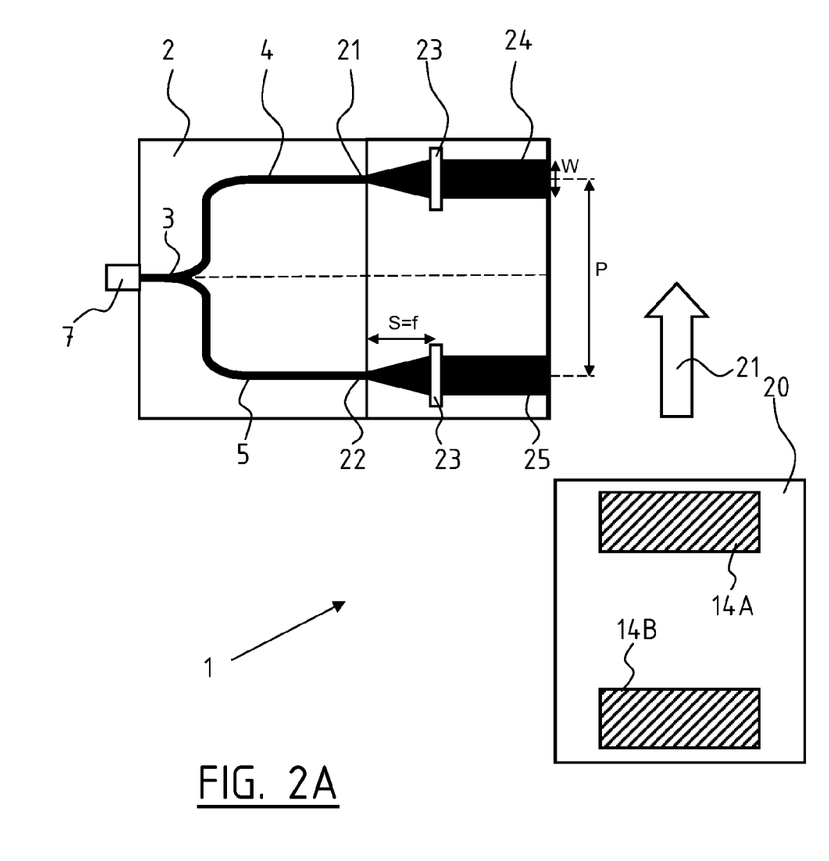
FIGS. 2A, 2B are a top view of a second embodiment of the sensor according to the invention, wherein a longitudinal section is shown separate from the sensor (1A) or in mounted position near an endzone of the sensor (1B)
Figure 2B:
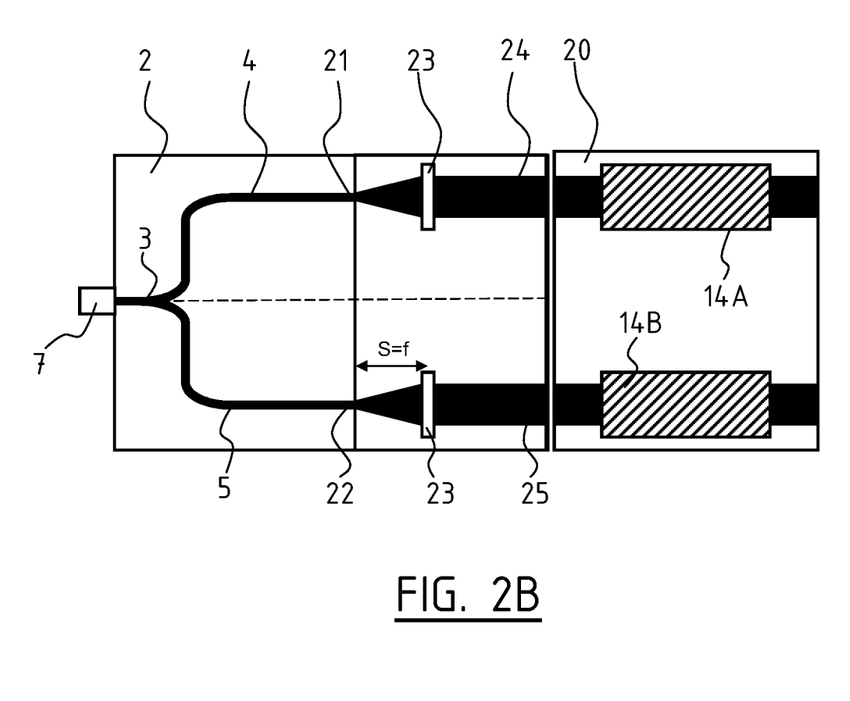
Figure 3:
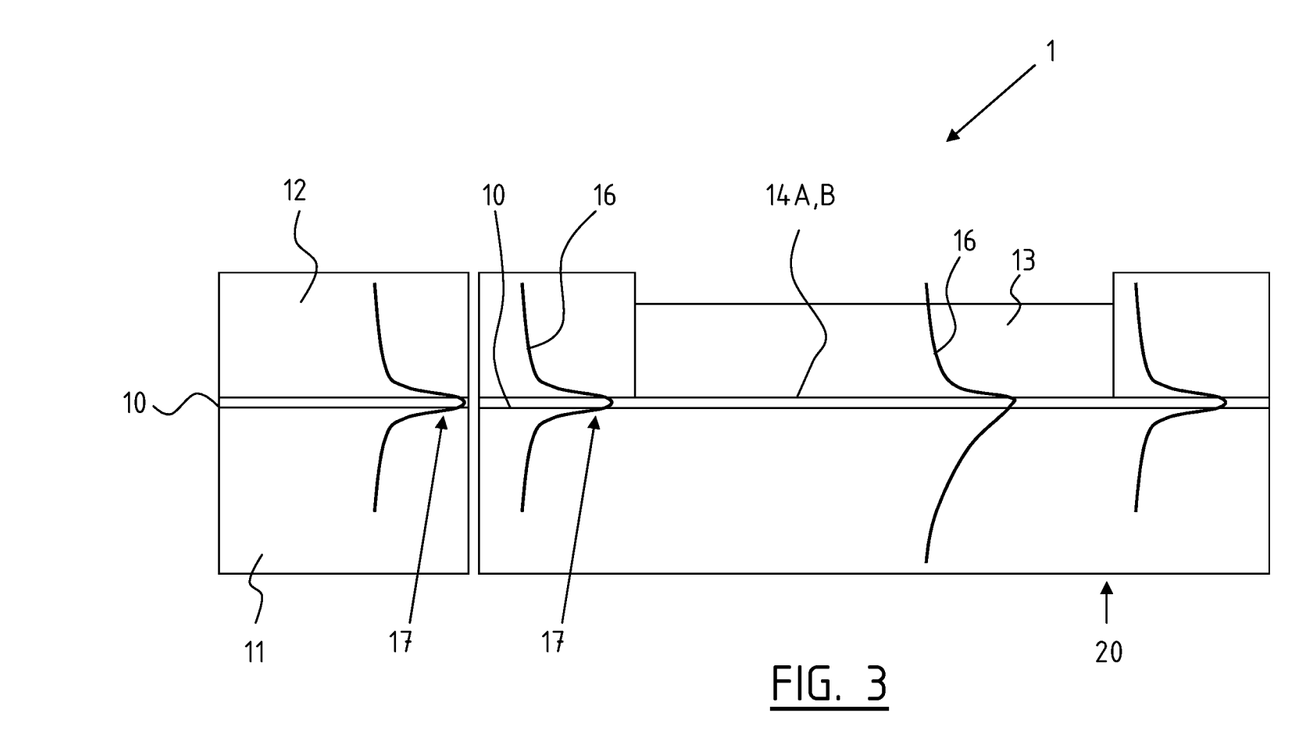
FIG. 3 is a cross section of the sensor of FIG. 2.

As is shown in FIGS. 1-3, the waveguide 3 and the two branches 4,5 comprise a waveguide core layer 10 sandwiched between two cladding layers formed by a lower cladding layer 11 and an upper cladding layer 12, of a lower refractive index than the waveguide core layer 10. In case of buried waveguides, the optical field is completely contained in the core and buffer layers and the propagation of light is not affected by environmental disturbances. By using etching techniques, the top cladding 12 is locally removed above the channel waveguides at well-defined positions in both branches 4, 5 of the sensor 1. In these so-called windows the evanescent field 16 of the light 17 that travels through the under-laying waveguides, extents into the environment above the sensor 1 and becomes susceptible to environmental changes. A sensing layer 13 that binds specifically with analyte molecules of interest is provided on the surface of the windows to form sensing sections 14A, 14B. When the sensing sections 14A, 14B are exposed to a sample material, specific binding of analyte molecules to the sensing layer 13 in the sensing sections 14A, 14B is probed by the evanescent field 16 of the light 17 travelling through the sensing branches 4, 5. This causes a change of the propagation speed of the light. As described before, the same analyte molecules may be sensed, thereby enhancing the accuracy, or different analyte molecules may be sensed, thereby having the opportunity to have multiple sensing at the same time. Optionally, one of the sensing layers 13 in the sensing sections 14A, 14B of branches 4, 5 show no specific binding, such that this branch may act as a reference branch. Because no specific binding occurs in the reference branch, the propagation speed of the light does not change, thus resulting in a phase difference between light coming from the sensing branch and the reference branch at the output waveguide 7. The induced phase difference is proportional to the amount of analyte molecules binding to the sensing layer 13.

As is shown in FIGS. 1A and 1B, a longitudinal section of said substrate 2 including said branches 4, 5 and said sensing sections 14A, 14B comprising said sensing layers 13 (see FIGS. 3-5) is exchangeable as a separate element 20. Said separate element 20 can be displaced between the position shown in FIG. 1A wherein the element 20 is separate from the sensor 1 and the position shown in FIG. 1A wherein the element 20 is located near a midzone of said sensor 1. The midzone is to be understood such that the separate element 20 is placed between two parts of the sensor 1, such that said two parts of the sensor 1 extend at opposite endzones of the separate element 20. The separate element 20 does not necessarily have to be placed in the middle of the sensor 1.

For optimal sensing with the sensor 1, the element 20 must be positioned correctly with respect to the midzone of said sensor 1, such that the light travelling through the two branches 4, 5 will travel through the sensing sections 14A, 14B and the sensing layers 13. In vertical direction, which is the direction into the drawing of FIG. 1, the correct positioning is relatively easy since the thicknesses of all layers on the substrate are known, such that the top surface of the upper cladding layer 12 of the sensor 1 can be used as a plane of reference for passive alignment. In the horizontal direction however, which horizontal direction is in the direction of the arrow 21, this is not the case. Therefore, the branches 4, 5 are only formed as channels over a part of said sensor 1, such that beams of light leaving the endzones 21, 22 of the channels will diverge.

Two lenses 23 are included in the branches 4, 5 at locations outside the channels and outside the element 20, such that in use the two diverging beams leaving the two channels and passing through respective lenses 23 are converted into parallel beams 24, 25, which parallel beams 24, 25 have a width that is larger than the width of the channels. Due to the increased width of the beams, a correct position of the element 20 wherein the beam will travel through the sensing sections 14A, 14B and the sensing layers 13 is provided. Third and fourth lenses 26 are included in the branches 4, 5 at the other end of the sensor 1 at locations outside the channels and outside the separate element 20, such that in use the two parallel beams passing through respective lenses 26 are converted into converging beams entering the channels of the branches 4, 5.

FIGS. 2A and 2B show another embodiment of the sensor 1 wherein the separate element 20 can be displaced between the position shown in FIG. 2A wherein the element 20 is separate from the sensor 1 and the position shown in FIG. 2B wherein the element 20 is located near an endzone of said sensor 1. The endzone is to be understood such that the separate element 20 is placed near one endzone of said sensor 1, such that the other endzone of the separate element 20 is the end of said sensor 1. As is clear from FIGS. 2A and 2B, light leaving the separate element 20 is not guided into another part of the sensor 1 as is the case with the sensor 1 of FIGS. 1A, 1B. The light leaving the sensor may be directed on a CCD camera such as in a Young interferometer or focussed on a light detector using an external lens.

Figure 4:
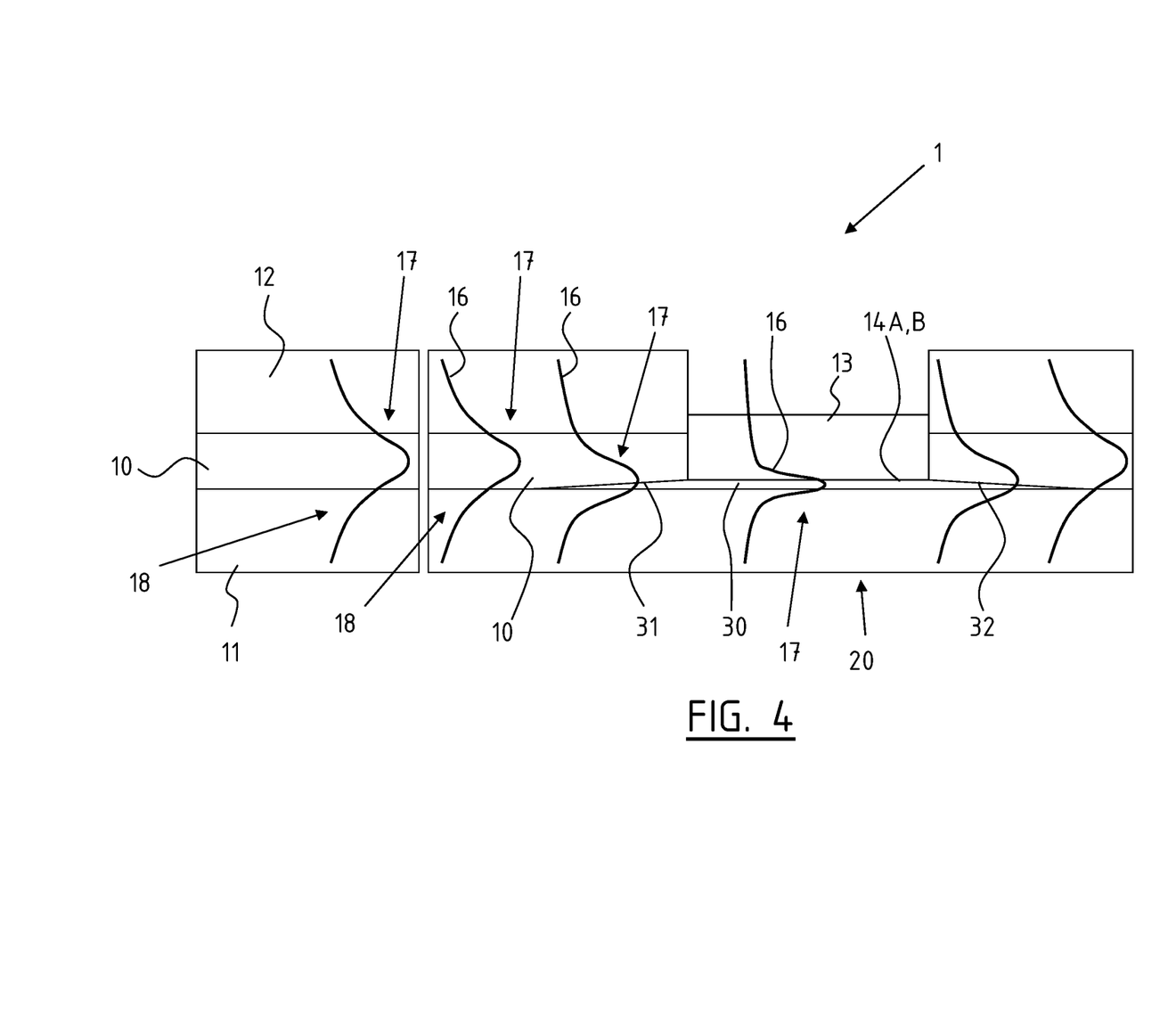
FIG. 4 is a cross section of a third embodiment of the sensor according to the invention

As is described above, the positioning of the element 20 in the vertical direction is relatively easy. However, as FIG. 4 shows, to enhance coupling of the light travelling through the branches 4, 5 into the separate element 20, the core layer 10 has an increased thickness with respect to the core layer 10 of FIG. 3. This increased thickness makes positioning of the separate element 20 easier. FIG. 4 also shows that the profile 18 of the light 17 does not change in the transfer to the separate element 20. However, the part 16 of the light 17 extending into the sensing layer 13 is relatively small. Therefore, the embodiment of the sensor 1 of FIG. 4 has a second core layer 30 included in the first core layer 10 in the separate element 20, which second core layer 30 has tapered endzones 31, 32. As is shown in FIG. 4, the part 16 of the light 17 extending into the sensing layer 13 is increased due to the smaller thickness of the second core layer 30. Due to the tapered endzones 31, 32, the light 17 is effectively guided into the second core layer 30.

Figure 5:
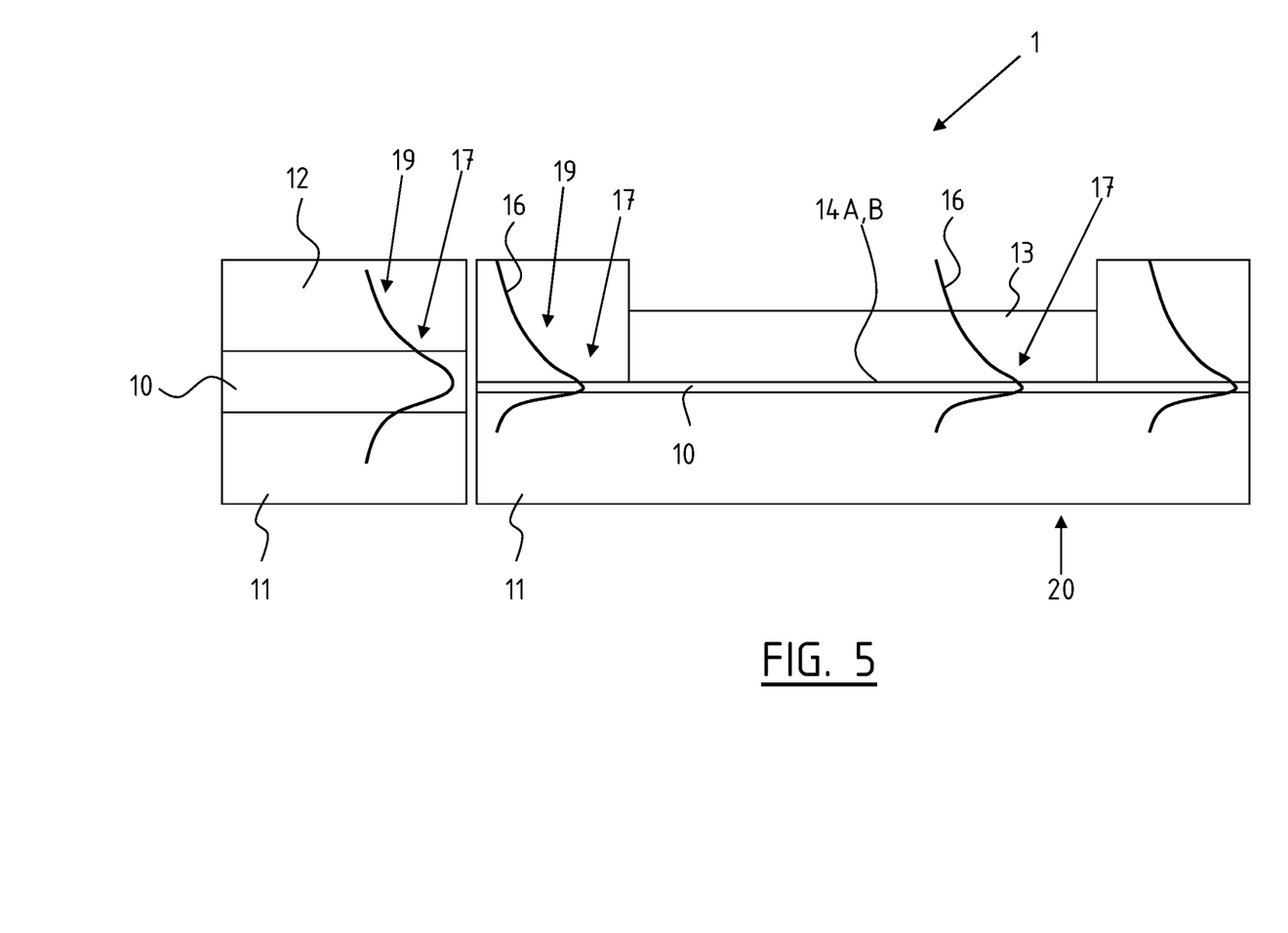
FIG. 5 is a cross section of a fourth embodiment of the sensor according to the invention.

FIG. 5 shows another embodiment of the sensor 1, wherein the coupling of the light travelling through the branches 4, 5 into the separate element 20 is enhanced. The lower cladding layer 11 of the separate element 20 of this embodiment of the sensor 1 has a refractive index that is lower than the refractive index of the upper cladding layer 12 and the sensing layer 13. Due to this lower cladding layer 11 with a lower refractive index, the light 17 is effectively guided into the core layer 10 of the separate element 20, because the profile 19 of the light 17 extending into the upper cladding layer 12 remains more or less the same. Also, the evanescent field extending into the sensing layers 13 is increased as compared to a sensor wherein the upper and lower cladding layers have the same refractive index or wherein the upper cladding layer has a refractive index that is higher. Due to the increased evanescent field extending into the sensing layers 13 the accuracy of the sensing is improved.

It is noted that in FIGS. 3-5 the cross-sections are shown for embodiments of the sensor 1 wherein the separate element 20 is located near the endzone of the sensor 1. It is clear that those cross-sections also apply to embodiments of the sensor 1 wherein the separate element 20 is located near the midzone of the sensor 1, but wherein the part of the sensor 1 extending at the opposite endzone of the separate element 20 is not shown.

Figure 6A:
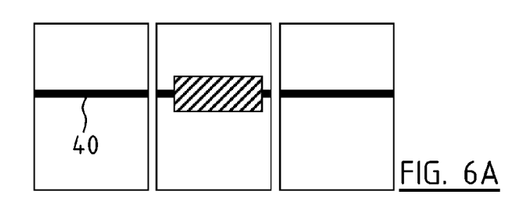
FIGS. 6A-6T are schematic representations of configurations of the sensor according to the invention.
Figure 6B:
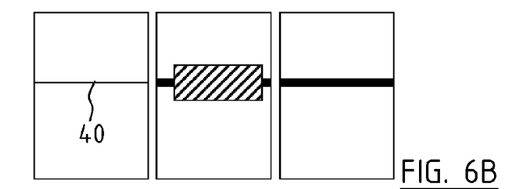
Figure 6C:
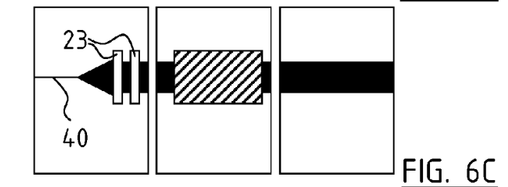
Figure 6D:
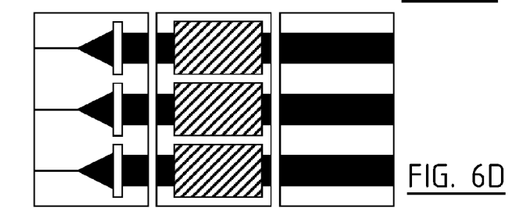
Figure 6E:
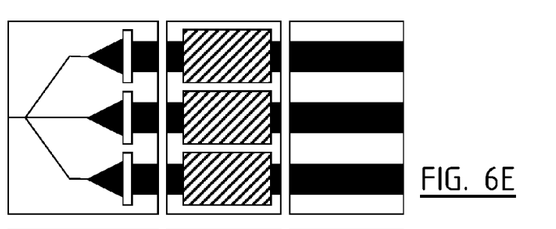
Figure 6F:
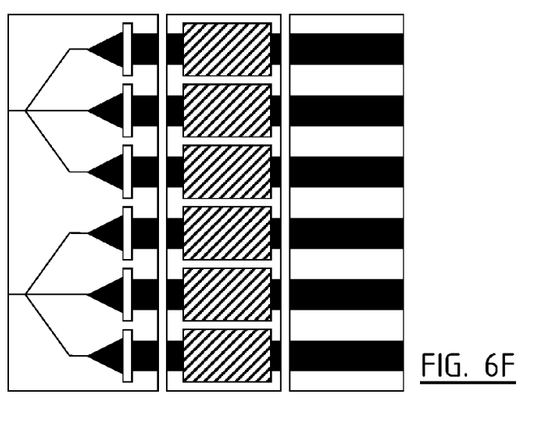
Figure 6G:
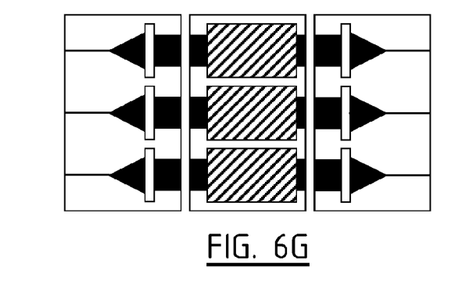
Figure 6H:
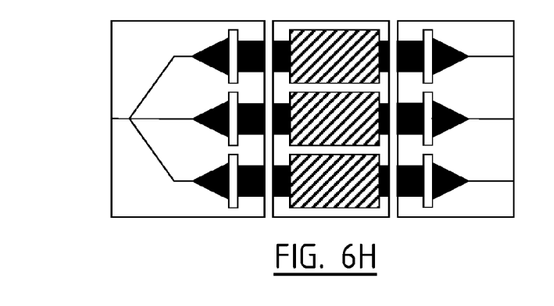
Figure 6I:
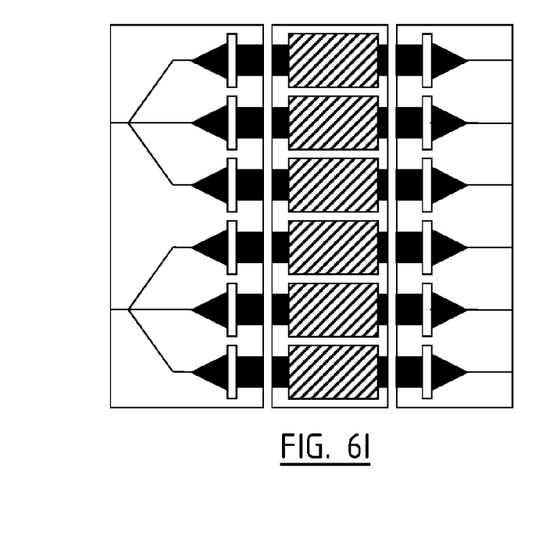
Figure 6J:
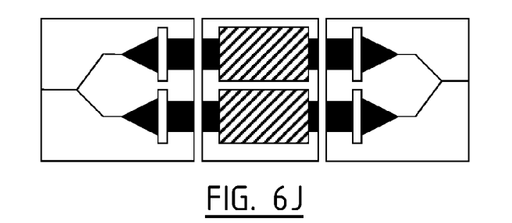
Figure 6K:
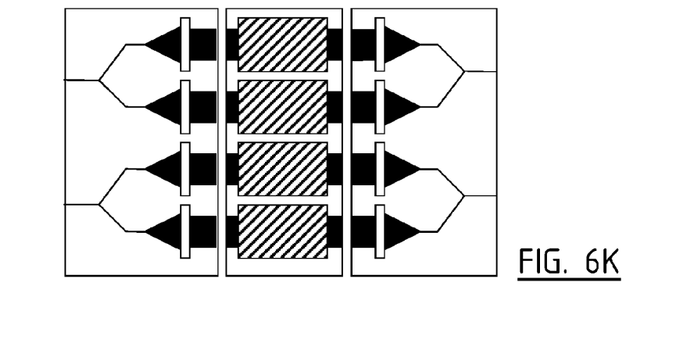
Figure 6L:
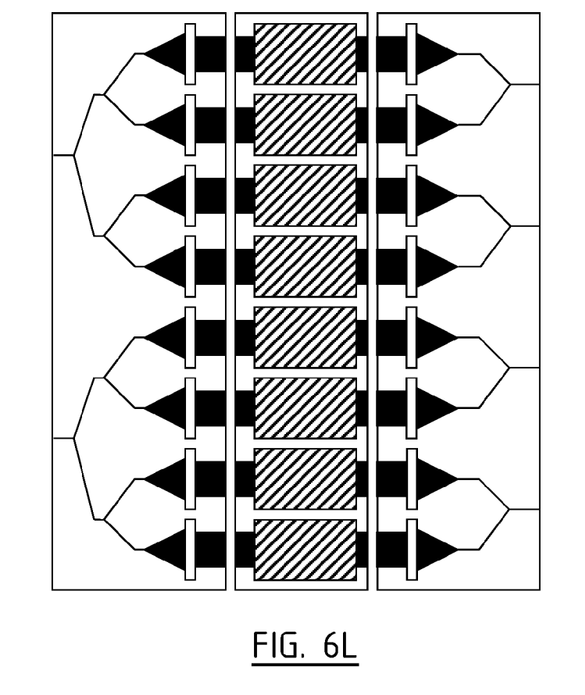
Figure 6M:
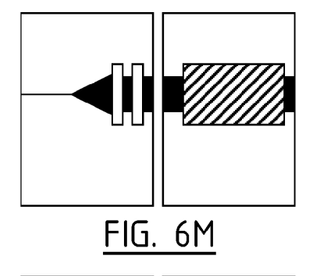
Figure 6N:
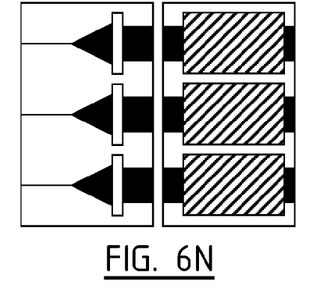
Figure 6O:
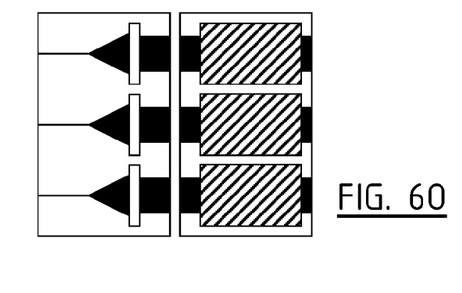
Figure 6P:
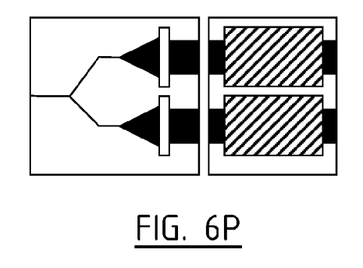
Figure 6Q:
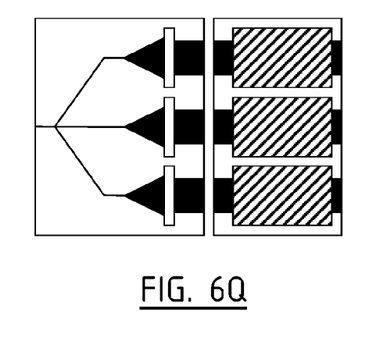
Figure 6R:
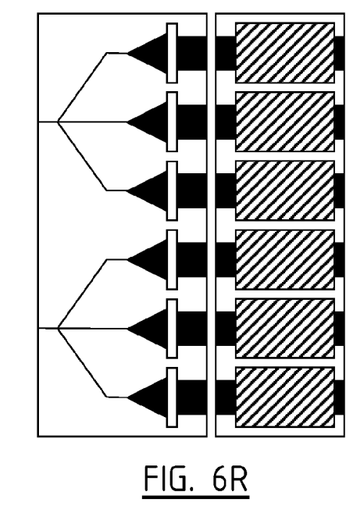
Figure 6S:
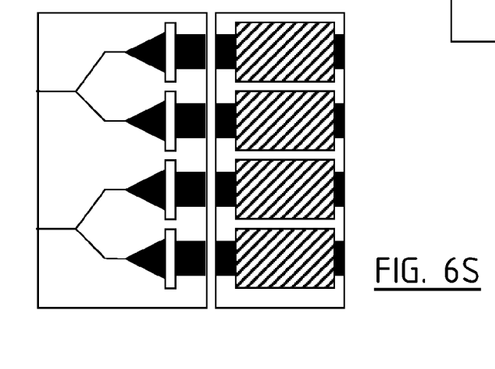
Figure 6T:
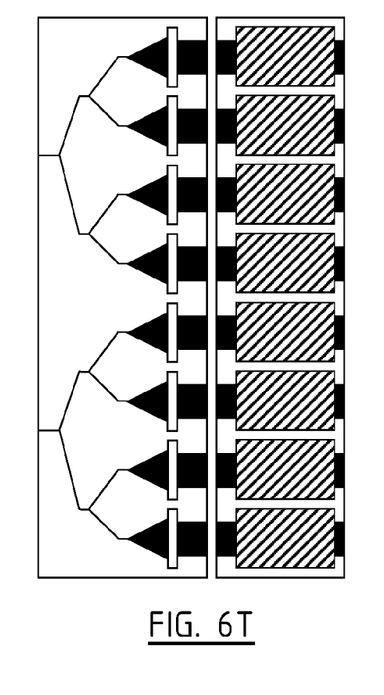

FIGS. 6A-T show several configurations of the sensor according to the invention. As appears from these figures, many configurations are possible. Therefore, it is clear that that these figures are not exclusive. Further, it is clear that all these possible configurations and/or not shown configurations fall within the scope of the appended claims. For clarity, the elements are numbered only in FIGS. 6A-6C.

FIG. 6A shows a configuration wherein the waveguide layer structure 40 is formed as a single path, which path has a width that is larger than the width of the channels shown in FIGS. 1 and 2. This is a cheap and simple configuration of the sensor according to the invention, because no lenses are needed.

FIG. 6B shows a configuration wherein the waveguide layer structure 40 is formed as a channel over a portion of its length. This is a cheap and simple configuration of the sensor according to the invention, because no lenses are needed.

FIG. 6C shows a configuration wherein the waveguide layer structure 40 is formed as a channel over a portion of its length. The sensor comprises an array of two lenses 23. An array of two or more lenses has the advantage that the diffraction losses are lower as compared to a single lens with the same power.

FIGS. 6D-6L show a plurality of configurations wherein the waveguide layer structure 40 is formed as multiple paths and/or channels. Multiple paths and/or channels have the advantages of multiple analyzing, improving the accuracy, or having a reference path or channel as described before.

FIGS. 6M-6T show a plurality of configurations wherein the separate element is located near an endzone of the sensor.

The invention is not restricted to the variants shown in the drawing, but it also extends to other preferred embodiments that fall within the scope of the appended claims.

The invention claimed is:

1. An integrated optical waveguide evanescent field sensor for sensing of chemical and/or physical quantities, comprising a substrate carrying a waveguide layer structure comprising:
    a waveguide core layer sandwiched between two cladding layers formed by a lower and a upper cladding layer, of a lower refractive index than the waveguide core layer,
    a sensing section comprising a sensing layer included in the upper cladding layer, wherein a longitudinal section of said substrate including said waveguide layer structure and said sensing section is exchangeable as a separate element, wherein the waveguide layer structure has a length and is formed as a channel over a portion of its length, wherein at least one lens is included in the waveguide layer structure located outside said channel and outside said separate element, such that a diverging beam leaving the channel and passing through the lens is converted into a parallel beam, which parallel beam has a width that is larger than the width of the channel.

2. The integrated optical waveguide evanescent sensor according to claim 1, wherein said separate element can be located near a midzone or an endzone of said sensor.

3. The integrated optical waveguide evanescent sensor according to claim 1, wherein said waveguide layer structure is formed as two parallel channels over said portion of its length, wherein two lenses are included in the waveguide layer structure located outside the channels and outside said separate element, such that in use two diverging beams leaving the two channels and passing through respective lenses are converted into parallel beams, which parallel beams have a width that is larger than the width of the channels.

4. The integrated optical waveguide evanescent sensor according to claim 3, wherein the substrate comprises a splitter for optically splitting a common input channel into said first and second channels at a first junction.

5. The integrated optical waveguide evanescent sensor according to claim 3, wherein said waveguide layer structure is formed as two parallel third and fourth channels over a second portion of its length, wherein a third lens and a fourth lens are included in the waveguide layer structure located outside the channels and outside the separate element, such that in use the two parallel beams passing through respective lenses are converted into converging beams entering said third and fourth channels.

6. The integrated optical waveguide evanescent sensor according to claim 5, wherein the substrate comprises a combiner for optically coupling said third and fourth channels into a common output channel at a second junction.

7. The integrated optical waveguide evanescent sensor according to claim 1, wherein the core layer in the separate element includes a second core layer with tapered endzones.

8. The integrated optical waveguide evanescent sensor according to claim 1, wherein the lower cladding layer of at least the separate element has a refractive index that is lower than the refractive index of the upper cladding layer and/or the sensing layer.

9. The integrated optical waveguide evanescent sensor according to claim 1, wherein said substrate is formed by said lower cladding layer as one integral part.

10. The integrated optical waveguide evanescent sensor according to claim 1, wherein the channel is a first channel at a first end of the substrate, wherein the waveguide layer structure further comprises a second channel at a second end of the substrate which is opposite the first end, and wherein the parallel beam extends from the first channel to the second channel.

11. A longitudinal section of a substrate for use in an integrated optical waveguide evanescent field sensor for sensing of chemical and/or physical quantities according to claim 1, said sensor comprising a substrate carrying a waveguide layer structure provided with a waveguide core layer sandwiched between two cladding layers formed by a lower and a upper cladding layer, of a lower refractive index than the waveguide core layer, a sensing section comprising a sensing layer included in the upper cladding layer, wherein said longitudinal section of said substrate including said waveguide layer structure and said sensing section is exchangeable as a separate element, wherein the waveguide layer structure has a length and is formed as a channel over a portion of its length, wherein at least one lens is included in the waveguide layer structure located outside said channel and outside said separate element, such that a diverging beam leaving the channel and passing through the lens is converted into a parallel beam, which parallel beam has a width that is larger than the width of the channel.

* * * * *